(12) United States Patent
To et al.

(10) Patent No.: US 12,150,649 B2
(45) Date of Patent: Nov. 26, 2024

(54) ENDOVASCULAR COIL AND METHOD FOR MAKING THE SAME

(71) Applicant: AVANTEC VASCULAR CORPORATION, Sunnyvale, CA (US)

(72) Inventors: John Thao To, Newark, CA (US); Ryan Masato Hoshino, San Diego, CA (US); Teresa Ruvalcaba, San Leandro, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 78 days.

(21) Appl. No.: 17/019,292

(22) Filed: Sep. 13, 2020

(65) Prior Publication Data

US 2021/0085334 A1 Mar. 25, 2021

Related U.S. Application Data

(60) Provisional application No. 62/900,012, filed on Sep. 13, 2019.

(51) Int. Cl.
*A61B 17/12* (2006.01)
*A61B 17/16* (2006.01)
(Continued)

(52) U.S. Cl.
CPC .... *A61B 17/12145* (2013.01); *A61B 17/1697* (2013.01); *B21F 3/02* (2013.01); *B21F 3/12* (2013.01); *A61B 2017/00526* (2013.01)

(58) Field of Classification Search
CPC ........ A61B 17/12145; A61B 17/12022; A61B 17/12131; A61B 17/1214; A61B 17/1697;
(Continued)

(56) References Cited

U.S. PATENT DOCUMENTS

| 5,645,558 A | 7/1997 | Horton |
| 6,254,592 B1 | 7/2001 | Samson et al. |

(Continued)

FOREIGN PATENT DOCUMENTS

| JP | 2004/500929 | 12/2001 |
| JP | 2007/525304 | 10/2005 |

(Continued)

OTHER PUBLICATIONS

WO, PCT/US20/50599 ISR and Written Opinion, Dec. 8, 2020.
European search report for EP 20863096.2, Jul. 20, 2022, Avantec Vascular Corporation—owned by applicant.

*Primary Examiner* — Erich G Herbermann
(74) *Attorney, Agent, or Firm* — Brian S. Boyer; SYNDICATED LAW, PC

(57) ABSTRACT

Disclosed are example embodiments of an endovascular coil having a twisted figure 8 shape. The endovascular coil includes: a first loop; a second loop; and an inflection region where a portion of the first loop transitions into a portion of the second loop. The second loop is rotated about an axis parallel to the longitudinal axis of the first loop to create the twisted figure 8 shape. The twist adds more randomness and variability to the filling behavior of the endovascular coil.

(Continued)

The added randomness and variability enables the twisted figure 8 coil to better fill the void of irregular-shaped aneurysms than other conventional embolic coils.

13 Claims, 17 Drawing Sheets

(51) Int. Cl.
    *B21F 3/02* (2006.01)
    *B21F 3/12* (2006.01)
    *A61B 17/00* (2006.01)
(58) Field of Classification Search
    CPC .......... A61B 17/0057; A61B 17/12027; A61B 17/12031; A61B 17/12036; A61B 17/1204; A61B 17/12113; A61B 17/12118; A61B 17/12122; A61B 17/12127; A61B 17/1215; A61B 17/12154; A61B 17/12163; A61B 17/12172; A61B 2017/00526; B21F 3/00; B21F 3/02; B21F 3/12; B21F 45/008
    See application file for complete search history.

(56) References Cited

U.S. PATENT DOCUMENTS

| | | |
|---|---|---|
| 6,638,291 B1 | 10/2003 | Ferrera et al. |
| 6,860,893 B2 | 3/2005 | Wallace et al. |
| 8,323,306 B2 | 12/2012 | Schaefer et al. |
| 10,081,048 B2 | 9/2018 | Honegger et al. |
| 10,307,168 B2 | 6/2019 | Morita |
| 2002/0107534 A1 | 1/2002 | Schaefer et al. |
| 2012/0041464 A1* | 2/2012 | Monetti ................ B21F 45/008 140/102.5 |
| 2017/0105738 A1 | 4/2017 | Suzuki |
| 2018/0263633 A1* | 9/2018 | Tsukumo ................ B21F 3/02 |
| 2018/0354020 A1 | 12/2018 | Monetti et al. |
| 2019/0142436 A1 | 5/2019 | Koyama et al. |

FOREIGN PATENT DOCUMENTS

| | | |
|---|---|---|
| JP | 2014/519886 | 11/2012 |
| WO | WO 2003/059176 | 7/2003 |
| WO | WO 2017/193375 | 11/2017 |

* cited by examiner

ENDOVASCULAR COIL AND METHOD FOR MAKING THE SAME

CROSS-REFERENCE TO RELATED APPLICATION

This application claims priority to U.S. Provisional Application No. 62/900,012, filed Sep. 13, 2019, which is hereby incorporated in its entirety by reference.

BACKGROUND

The treatment of aneurysms and other similar vascular disorders often involves the placement of endovascular coils within a space of an aneurysm or other vascular structure. In an aneurysm, this space is often spherical. However, in some instances, it can be elliptical or can have two or more lobular protrusions (often called bi-lobed or multi-lobed aneurysms). Conventional coil systems have a variety of shapes and types of coil such as framing, filling, and finishing coils.

A framing coil is typically the first coil placed within an aneurysm and has a complex or three-dimensional shape designed to fit within the space formed by the aneurysm. The framing coil can be used to perform the following functions: (1) provide a stable frame within the confines of the aneurysm into which subsequent coils can be placed; (2) provide adequate loop coverage across the neck of the aneurysm; and (3) prevent loops from crossing the center of the aneurysm (which can create compartments within the aneurysm that require additional catheter manipulation, prolonging the procedure and increasing the risk of aneurysm rupture).

Additionally, in some instances, it is desirable for the framing coil to be delivered with minimally or acceptably low friction within a microcatheter. Many framing coils have spherical shapes that can perform these functions when treating a spherical aneurysm; however, they are often inadequate when the aneurysm is non-spherical (e.g. elliptical or bi-lobed). Other framing coils have complex shapes that fit within non-spherical aneurysms; however, such coils typically consist of loops that are arranged with independent axes and are designed to be constrained by the aneurysm itself. This type of shape results in a framing coil with significant potential energy. This means that in its unrestrained state, the framing coil tend to expand well beyond the dimensions of the aneurysm and therefore transfers force directly to the aneurysm wall when constrained in the space. While this force may not be enough to harm the aneurysm wall, it leaves the framing coil in a state susceptible to movement upon placement of subsequent coils. Often times, such coils will shift and potentially cause a loop to protrude into the parent artery, which requires adjunctive and/or emergency therapy. Additionally, the complex shapes of some framing coils often increase the friction created when they are delivered through a microcatheter.

Endovascular coils, whether they are framing, filling, or finishing coils, with complex 3D shapes do not fill various irregularly-shaped and multi-lobed aneurysms well as they are designed and heat set to form very specific 3D shapes. As such, conventional complex-shaped endovascular coils can leave an area or a volume of an aneurysm unfilled when the shape of the aneurysm does not match well with the complex shape of the coils. Understandably, there is a chance that a randomly selected complex-shaped coil can fill an irregularly-shaped aneurysm to a reasonable acceptable degree. However, a properly designed and engineered an endovascular coil can predictably and reliably fill any irregularly-shaped aneurysms and thereby relying less on chances for a successful procedure. Accordingly, what is needed is an endovascular coil that would fill any irregularly-shaped and multi-lobed aneurysms in a predictable, reliable, and substantially complete manner.

SUMMARY

Disclosed are example embodiments of an endovascular coil having a twisted figure 8 shape. The endovascular coil includes: a first loop; a second loop; and an inflection region where a portion of the first loop transitions into a portion of the second loop.

The second loop is rotated about a first axis by a first degree of rotation. The first axis is substantially parallel to a major axis of the first loop. The first degree of rotation can range between 5-90 degrees. In some embodiments, the first degree of rotation is 45 degrees. The first and second loop of the endovascular coil can be disposed in a figure 8 pattern.

The second loop can be further rotated about a second axis by a second degree of rotation. The first and second axes are non-parallel to each other but are both located on the primary plane of the first loop, which is the plane where the first loop is disposed. The second degree of rotation of the second loop can have a range between 5-45 degrees. This causes the second loop to be twisted about the longitudinal axis of the figure 8 while also being offset at a certain angle from the same reference axis.

In some embodiments, the second loop can have an undulating tracing pattern that dips above and below a primary plane of the second loop. The tracing pattern can break and cross the primary plane of the second loop at multiple locations. The endovascular coil can also have the first loop with a first cross-section and the second loop with second cross-section. The first and second cross-section can be the same or they can be different. The cross-section can have a shape of a circle, a polygon, or an ellipse. The second loop can also be made with wire having a smaller diameter than the wire of the first loop.

The inflection region of the endovascular coil can be twisted and overlapped. In the inflection region, a portion of the first loop can overlap and touch a portion of the second loop such that both loops are closed loops. Alternatively, the portion of the first loop can twist, overlap, but do not touch each other—leaving the inflection region as an open region.

The endovascular coil can have multiple first and second loop pairs. Each loop pair is continuously connected at the inflection region and stacks over the previous and/or next loop pair. The endovascular coil can have many loop pairs (e.g., 2-100). One or more loop pairs formed by the distal end of the endovascular coil can have a different wire attribute. For example, the endovascular coil can have a total length of 40 cm, the last 5-10 cm can have a different wire attribute. A wire attribute can be the wire stiffness, cross-sectional shape, diameter, or other external feature such as fibrous extensions/protrusions. A loop pair comprises a first and a second loop.

One of the first and second loops can have one or more stress points integrated into the loop. The one or more of the stress points can include a bending radius between 0.001 to 0.5 of a radius of the first or second loop.

Also disclosed is an embolic coil that includes: a first loop having a first major axis; and a second loop connected to the first loop, the second loop having a second major axis, wherein the first and second major axis are substantially parallel to each other, and wherein the second loop is rotated about the second major axis, and wherein the first and second loops form a twisted figure 8 shape.

Also disclosed is a method for fabricating an endovascular coil. The method includes: securing a first end of a coil wire to a first rod of a mandrel, wherein the mandrel comprises the first rod and a second rod; routing the wire around the first and second rods to create multiple figure 8 wire patterns on the first and second rods; rotating one of the first and second rods about a point of rotation by a first degree of rotation, wherein the point of rotation is substantially located on a longitudinal axis of one of the multiple figure 8 wire patterns; and heat setting the multiple figure 8 wire patterns while being rotated in the mandrel by the first degree of rotation.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the disclosed subject matter.

BRIEF DESCRIPTION OF THE DRAWINGS

The foregoing summary, as well as the following detailed description, is better understood when read in conjunction with the accompanying drawings. The accompanying drawings, which are incorporated herein and form part of the specification, illustrate a plurality of embodiments and, together with the description, further serve to explain the principles involved and to enable a person skilled in the relevant art(s) to make and use the disclosed technologies.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

DETAILED DESCRIPTION

Overview

Figure 8:
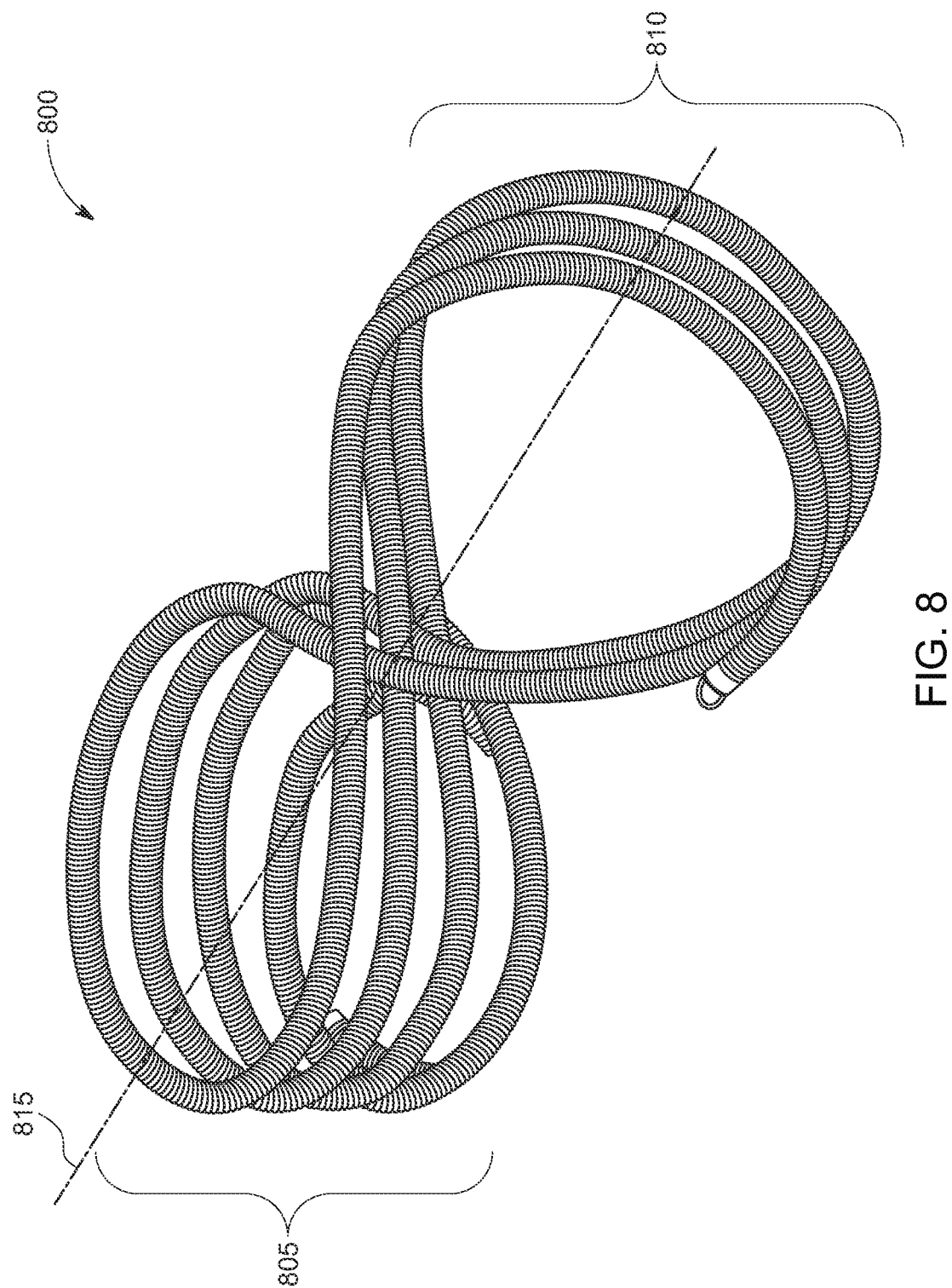
FIG. 8 illustrates a twisted figure 8 endovascular coil having multiple stacked loops in accordance with some embodiments of the present disclosure.

Disclosed herein is an endovascular/embolic coil that exhibits a twisted figure 8 shape. The figure 8 shape have two round portions that form the upper and lower portions of the figure 8 shape. In the twisted figure 8 coil, one of the round portions is twisted or rotated with respect to the other non-rotated round portion. The rotated round portion can be rotated by any degree of rotation such as, but not limited to, a range between 1-179 degrees. In some embodiments, the rotated round portion is rotated by 45 degrees. In another example, the rotated round portion is rotated by 90 degrees. The round portions of the figure 8 coil can be circular, polygonal, or elliptical.

In some embodiments, the rotated round portion is rotated about an axis that is substantially parallel to the semi-major axis of the non-rotated round portion. If the non-rotated round portions are circular, then the semi-major axis is the diameter. In this case, the rotated round portion is rotated about a common or longitudinal axis of the two round portions. Stated differently, the rotated round portion is rotated about the longitudinal axis of the straight figure 8, which is the common major axis of both round portions. More detail on the relative position and rotation of the round portions of the figure 8-shaped coil is provided below.

The embolic coil is configured to have a twisted figure 8 shape in its minimum energy state or secondary configuration. When the embolic coil is uninhibited by a sleeve or catheter, the coil is configured to revert to its secondary configuration to obtain a minimum energy state, which is in a shape of a twisted figure 8. When the embolic coil is dispensed on a flat surface (outside of the body), the coil forms multiple layers of figure 8s stacking on top of each other while appearing to be generally flat—not rotated or twisted. This is due to the restriction of the flat surface and gravity pulling the rotated round portion of the embolic coil toward the flat surface. When deployed inside the body (e.g., inside an aneurysm), the same embolic coil will have a twisted figure 8 shape (see for example FIG. 1). Bodily fluid inside of the aneurysm or artery provides some a buoyancy and thereby suspending the embolic coil and allowing it to form its minimum energy state and shape, which is a twisted/rotated figure 8 shape. Empirical data show that the twist adds more randomness and variability to the filling behavior of the coil as it fills an aneurysm (e.g., an irregular-shaped (e.g., multi-lobes) aneurysm). The added randomness and variability of the filling behavior enables the twisted figure-8 embolic coil to better fill the void of irregular-shaped aneurysms than other conventional embolic coils such as straight figure 8 shaped coils.

In some embodiments, the twisted figure 8 coil can have multiple portions such as, but not limited to, a proximal portion and distal portion. The distal portion can be made with a different material or the same material but with different attributes such as, but not limited to, stiffness (e.g., diameter, thickness), softness, and other external features (e.g., fiber protrusions). In some embodiments, distal portion can be thinner and more pliable than the proximal portion. Conversely, the proximal portion can be thinner and more pliable than the distal portion.

Twisted Figure 8

FIG. 1 illustrates an endovascular coil 100 with a twisted figure 8 shape in accordance with some embodiments of the present disclosure. Endovascular coil 100 includes a first loop 105 and a second loop 110. First loop 105 is disposed on a first plane 115. Second loop 110 is disposed on a second plane 120, which is at an offset angle with respect to first plane 115. The offset angle between first plane 115 and second plane 120 can range between 1 to 179 degrees. In some embodiments, the offset angle is approximately 90 degrees. In another embodiment, the offset angle is 45 degree. As shown, the offset angle is the angle in which second loop 110 is rotated about longitudinal axis 130, which is a common axis of both first and second loops 105, 110. In some embodiments, the offset angle can be an angle of rotation about a second axis of second loop 110. The second axis (not shown) can be the same as axis 130 or it can be substantially parallel to axis 130. The second axis can be a semi-major axis of loop 110 in the case where loop 110 is elliptical. The second axis can be the longitudinal axis of the overall coil.

Figure 1A:
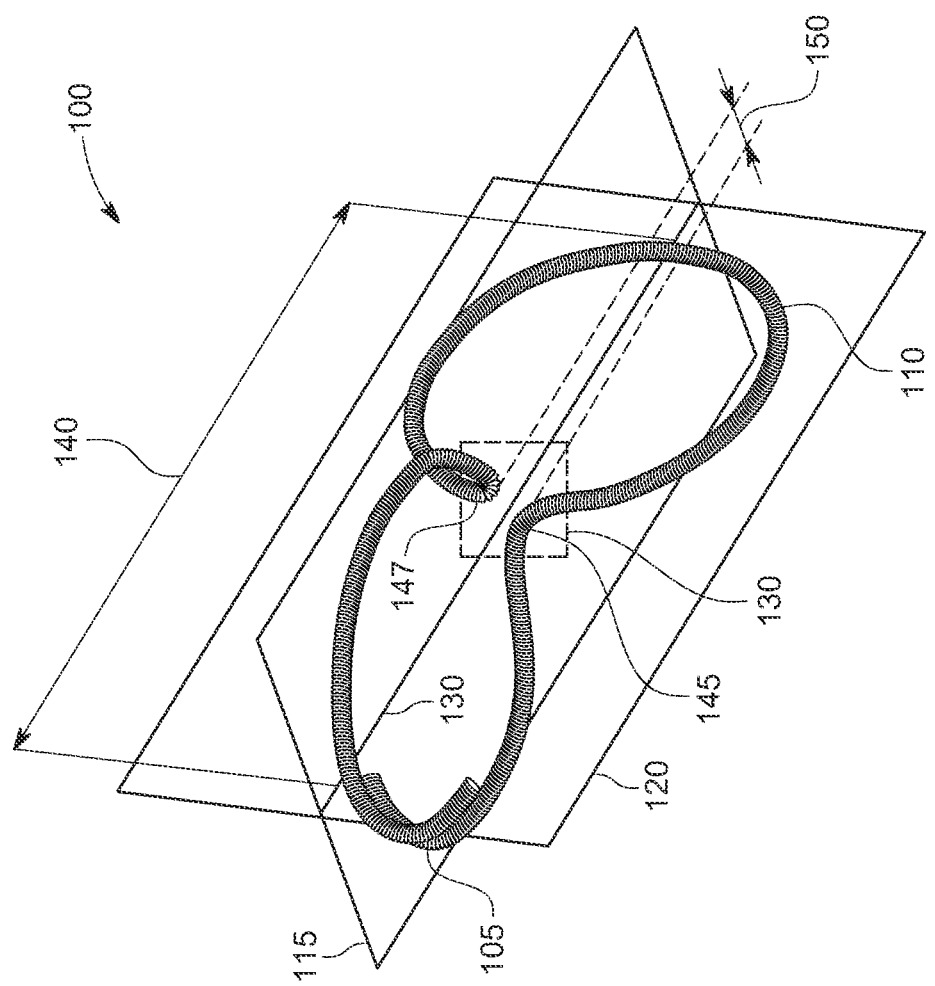
FIGS. 1A and 1B illustrate endovascular coil having two loops in different planes in accordance with some embodiments of the present disclosure.
Figure 1B:
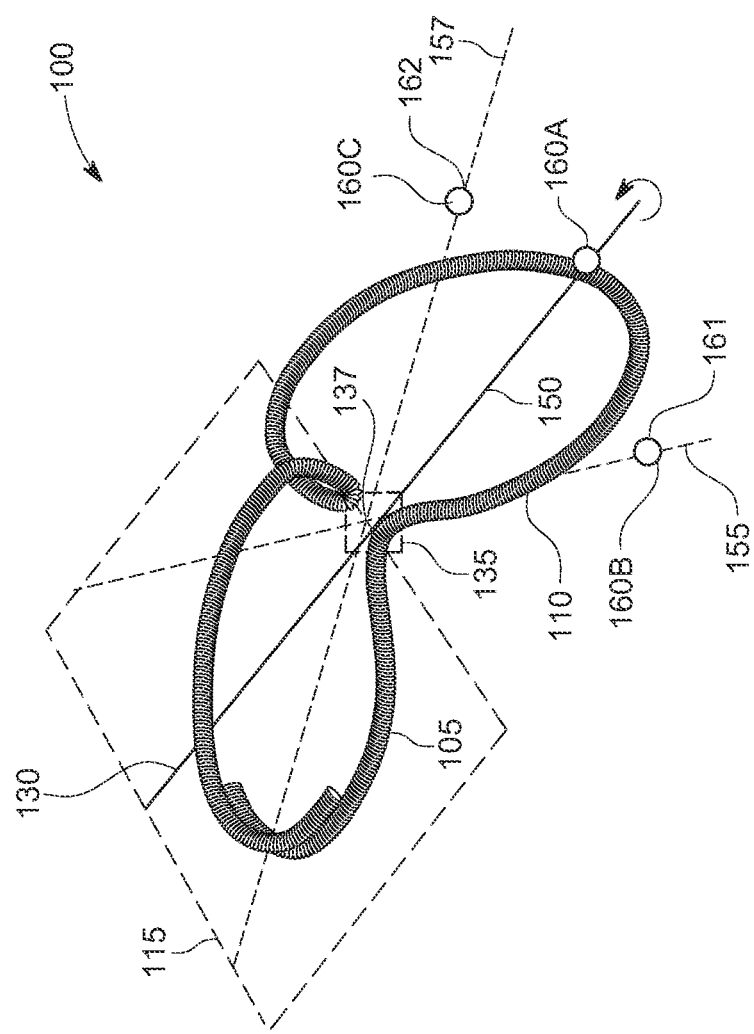

FIG. 1B illustrates endovascular coil 100 in a different reference environment to help illustrate the spatial relationship of the loops of the twisted figure 8 coil. The spatial relationship between first and second loops 105, 110 can be defined by plane 115 upon which first loop 105 is disposed and an axis of rotation 150 of second loop 110. Axis of rotation 150 is disposed on plane 115 and can be substantially parallel to the main axis and diameter of first loop 105. Axis of rotation 150 can also be the same major axis for first loop 105. In other words, axis 150 can be the same as longitudinal axis 130 of coil 100. As shown, second loop 110 is rotated about axis of rotation 150 by 90 degrees. However, second loop 110 can be rotated by any degrees about axis 150 such as, but not limited to, 5, 10, 20, 25, 30, 35, 40, 45, 50, 55 and 60 degrees.

In some embodiments, after second loop 110 is rotated about axis 150, second loop 110 can be further pivoted about inflection region 135 or focal point 137 by 1 to 90 degrees. For example, second loop 110 at the position shown in FIG. 1B can be pivoted such that the loop body is aligned with axis 155 or 157. For instance, second loop 110 can be pivoted such that distal point 160A of second loop 110 is translated to location 161 on axis 155, which is the same location as distal point 160B. Similarly, second loop 110 can be pivoted such that distal point 160A of second loop 110 is translated to location 162 on axis 157, which is the same location as distal point 160C.

Stated differently, the twisted figure 8 coil 100 can be formed starting with both loops 105, 110 in substantially the same plane. For the purpose of illustration, let us assume that coil 100 is standing vertically with first loop 105 at the top and second loop 110 at the bottom. To form the twisted figure 8 shape, first or upper loop 105 is held in place while second or bottom loop 110 is twisted about longitudinal axis 130. As mentioned, the angle of rotation can be any degrees. As shown, the angle of rotation is 90 degrees. During a manufacturing stage of twisted figure 8 coil 100, multiple figure 8 coils can be formed and twisted at the same time using a special mandrel. More description on the coil wrapping and heat setting procedures for fabricating twisted figure coil 100 is provided below (see FIGS. 10A-H).

Figure 2A:
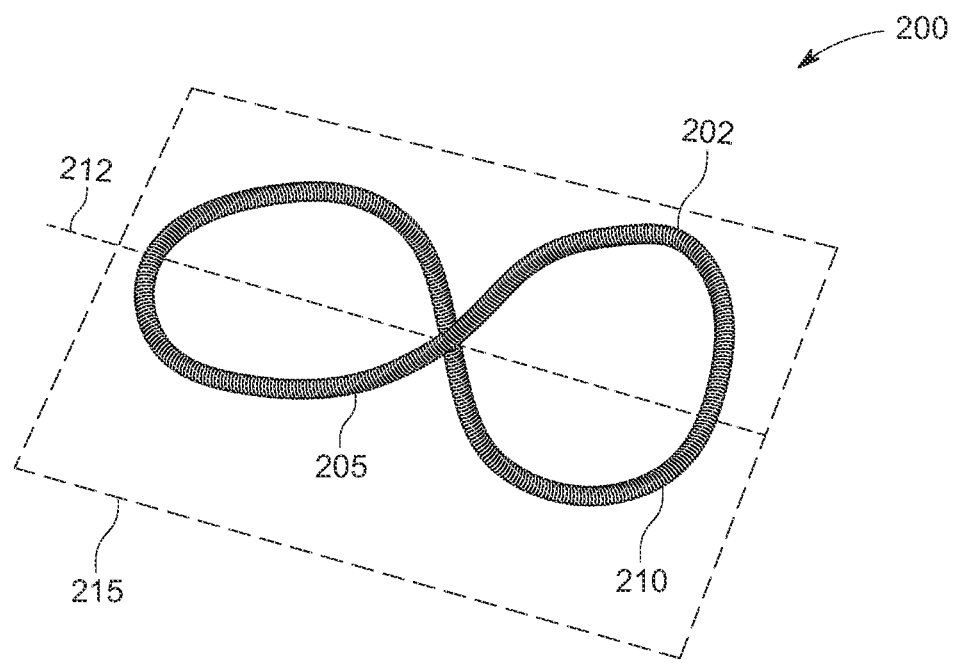
FIGS. 2A, 2B, and 2C illustrate a process for fabricating an endovascular coil in accordance with some embodiments of the present disclosure.
Figure 2B:
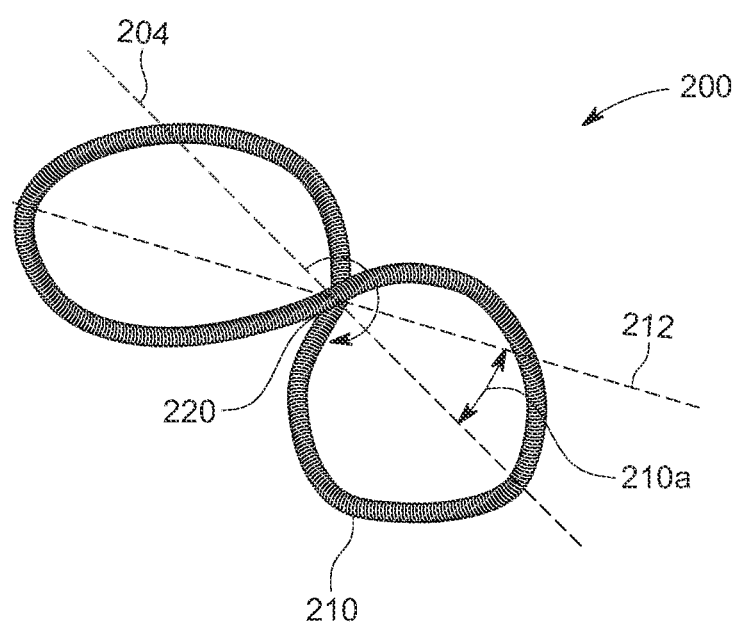
Figure 2C:
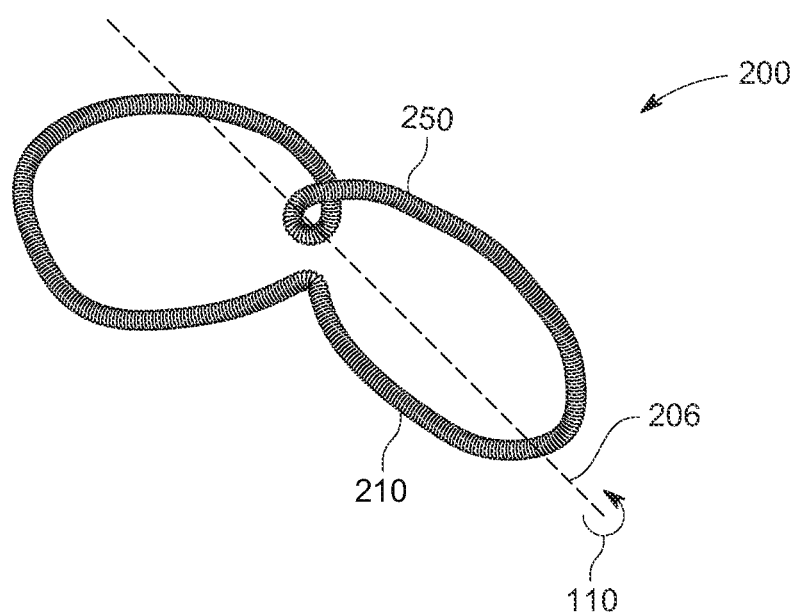

FIGS. 2A-C illustrate a process 200 for fabricating a twisted figure 8 coil 250 in accordance with some embodiments of the present disclosure. FIG. 2A illustrates a straight figure 8 coil 202 with first loop 205 and second loop 210 being substantially on the same plane 215. Process 200 starts by offsetting second loop 210 with respect to longitudinal axis 212 by any amount of degree such as between 1-90 degrees while staying substantially on the same plane 215. For example, second loop 210 can be twisted about focal point 220 until a desired offset angle is reached (e.g., 15, 20, 30, 45). All the while the primary plane of second loop 210 is substantially parallel to plane 215. As shown in FIG. 2B, angle 225 is approximately 28.4 degrees and second loop 210 is still substantially parallel to plane 215. In this example, axis 204 is the major axis of second loop 210.

Next, loop 210 is then rotated about axis 204 by a desired degree of rotation (e.g., 2, 10, 45, 90). This creates the twisted figure 8 coil 250 as second loop 210 is both twisted and offset. It should be noted that twisted figure 8 coil 250 can also be formed by first rotating second loop 210 about axis 212 (by any degree of rotation) and then offsetting the rotated coil as shown in FIG. 2B. The end result is the same coil 250 as shown in FIG. 2C.

The first loop (e.g., 105, 205) can have approximately the same diameter as the second loop (e.g., 110, 210). The diameter of first loop ($M_{oo}$) can be smaller than the diameter of the second loop ($D_{loop2}$). In some embodiments, the first loop can have a larger diameter than the second loop ($D_{loop1} > D_{loop2}$). The first and second loops can be circular, polygonal, or elliptical. In some embodiments, the first and second loops can have a different loop shape such as an ellipse or a polygon (e.g., hexagon and decagon). For example, the first loop (e.g., 105, 205) can be circular and the second loop (e.g., 110, 210) can be polygonal. In another instance, the first loop (e.g., 105, 205) can have an elliptical shape and the second loop (e.g., 110, 210) can have a hexagonal shape.

The cross-sectional shape of the first and second loops 105 and 110 can be the same. Alternatively, the cross-sectional shape of the first and second loops 105 and 110 can be different. For example, first loop 105 can have a circular cross-sectional shape and second loop 110 can have a hexagonal cross-sectional shape. The coil thickness (diameter of the cross-section) of the first and second loops 105 and 110 can be the same. In some embodiments, the coil thickness of the first and second loops 105 and 110 can be different. For example, the first loop can have a larger outer diameter than the second loop. For example, the first loop can have an outer diameter of 0.00257" and the second loop can have an outer diameter of 0.002".

Additionally, twisted figure 8 coil 100 and 250 can have two different portions, a proximal and a distal portion. The proximal portion can have a total length of 20-40 cm, and the distal portion can have a total length of 3-10 cm. Each portion can have multiple twisted figure 8 coils. Although coils 100 and 250 are shown individually (for illustrative purposes), coils 100 and 250 can have multiple coils connected to each other as shown in FIG. 11.

Referring again to FIG. 1A, in some embodiments, endovascular coil 100 and/or 250 can have an end-to-end length 140 that is coincident with axis 130 and is substantially equal to the sum of the diameters of the first and second loops 105 and 110 (Dloop1+Dloop2). Length 140 of coil 100 can be greater than Dloop1+Dloop2. In this embodiment, transitional portion 131 can have an offset distance between the loops. The offset can be tangential to one of the loops. End-to-end length 140 can be less than Dloop1+Dloop2. For example, length 140 can be 0.5 times the sum of the diameters of loops 105 and 110 (0.5×(Dloop1+Dloop2)). Length 140 can be larger than 2 times the sum of the diameters of loops 105 and 110 (2×(Dloop1+Dloop2)). In some embodiments, length 140 can range between 0.6× (Dloop1+Dloop2) and 1.4×(Dloop1+Dloop2). In one embodiments, length 140 can range between 0.75×(Dloop1+Dloop2) and 1.25×(Dloop1+Dloop2).

In some embodiments, axis 130 can also be curved or angled. The curve can be gradual from end-to-end of coil 100. Alternatively, the curve can be abrupt starting at transitional portion 131. Axis 130 can be curve or angle such that tangents of loop 105 and loop 110 can be parallel or perpendicular (0-90 degrees) to each other. In some embodiments, the tangents of loop 105 and loop 110 are 45 degrees with respect to each other.

Each loop 105 or 110 can have multiple loops stacked together (see FIG. 10). The shape of each loop in the stack can be substantially the same. Alternatively, the shape of each look within a stack can be different. For example, loop 105 can have 3 loops stacked together. The first loop can be circular, the second loop can be elliptical, and the third loop can be polygonal. Loop 150 can have 4 loops stacked together, and one or more loops can be located at an offset from the main plane (e.g., plane 115) as shown in FIGS. 1A and 2C.

In some embodiments, the transition or inflection portion 131 includes a waist area, which is the area where loop portions 145 and 147 is the closest to each other. A waist gap 150 is the distance between the loop portions 145 and 147. In some embodiments, the size of gap 150 can range from 0 (touching or overlapping) to half of the diameter of loop 105 or loop 110. The size of gap 150 can be substantially the same as the diameter of the wire coil of loop 105. In some embodiments, gap 150 can range between $0.1×(D_{loop1})$ and $0.8×(D_{loop1})$. For example, gap 150 can be 0.3 times $D_{loop1}$ or $D_{loop2}$. Gap 150 can also range between $0.1×(D_{loop2})$ and $0.8×(D_{loop2})$. As noted, $D_{loop1}$ can be different than $D_{loop2}$.

In some embodiments, loop 105 can be form on a mandrel with loops 105 and loop 110 are initially parallel (being on the same plane). Then prior to heat shaping, the mandrel can be rotated to adjust the angle relative to loops 105 and 110. The mandrel is configured to be rotatable such that the angle relative to loops 105 and 110 can be adjusted between 5-175 degrees. For example, the mandrel can be rotated between 30-90 degrees prior to heat shaping. Endovascular coil 100 can be made of a shape retentive metal alloy such as Nitinol. Other suitable bio-compatible metals and/or metal alloys can also be used (e.g., stainless steel, platinum) to fabricate coil 100.

Figure 3:
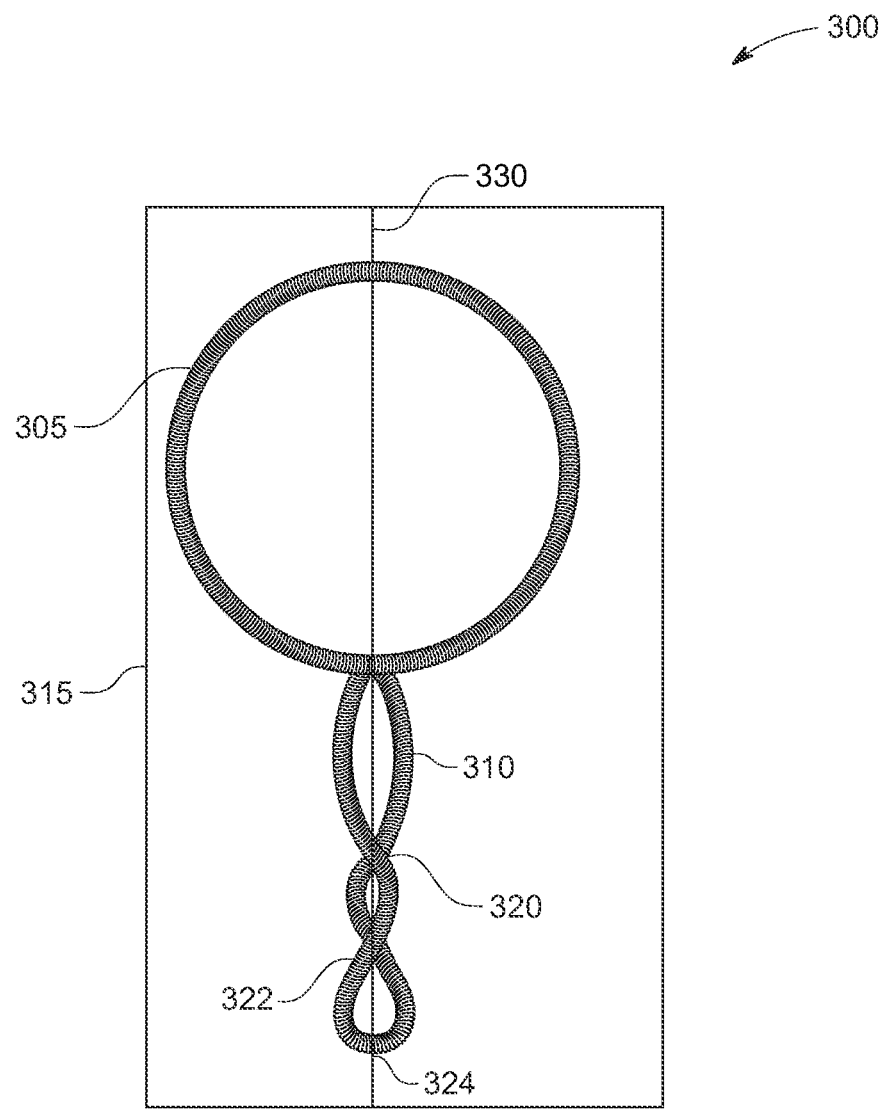
FIG. 3 illustrates an endovascular coil having at least one loop with an undulating shape in accordance with some embodiments of the present disclosure.

FIG. 3 is a top view of coil 300 in accordance with some embodiments of the present disclosure. Coil 300 can have one or more features and attributes of coils 100 and 250 as described with respect to FIGS. 1A-1B and 2A-2C. Coil 300 is a twisted figure 8 coil with bottom loop 310 rotated about longitudinal axis 330 at approximately 90 degrees. Although loop 310 is shown to be rotated at 90 degrees, it can be rotated at any desired degree such as 15, 20, 25, 35, 40 and 45 degrees.

As shown, coil 300 includes upper loop 305 and bottom loop 310. Loop 305 can be disposed substantially on plane 315, and loop 310 can be disposed substantially on plane 315. Loop 310 can have an undulating tracing pattern that dips above and below plane 315. For example, when tracing the entire circumference of loop 310 at any starting point, the traced path (as it follows the circumference of loop 310) would break plane 315 at several locations when the entire loop is traced. In some embodiments, loop 310 breaks plane 235 at least 2 times on the left and at least 2 times on the right. For example, loop 310 can break plane 235 at three different locations 320, 322, and 324. In some embodiments, loop 305 and/or 210 can have an overall circular or polygonal shape such as a hexagon or decagon. Although not obvious from FIG. 3, loop 305 can also undulate above and below plane 315 as it traces out a circular shape as shown. Alternatively, loop 305 can be substantially flat.

Figure 4:
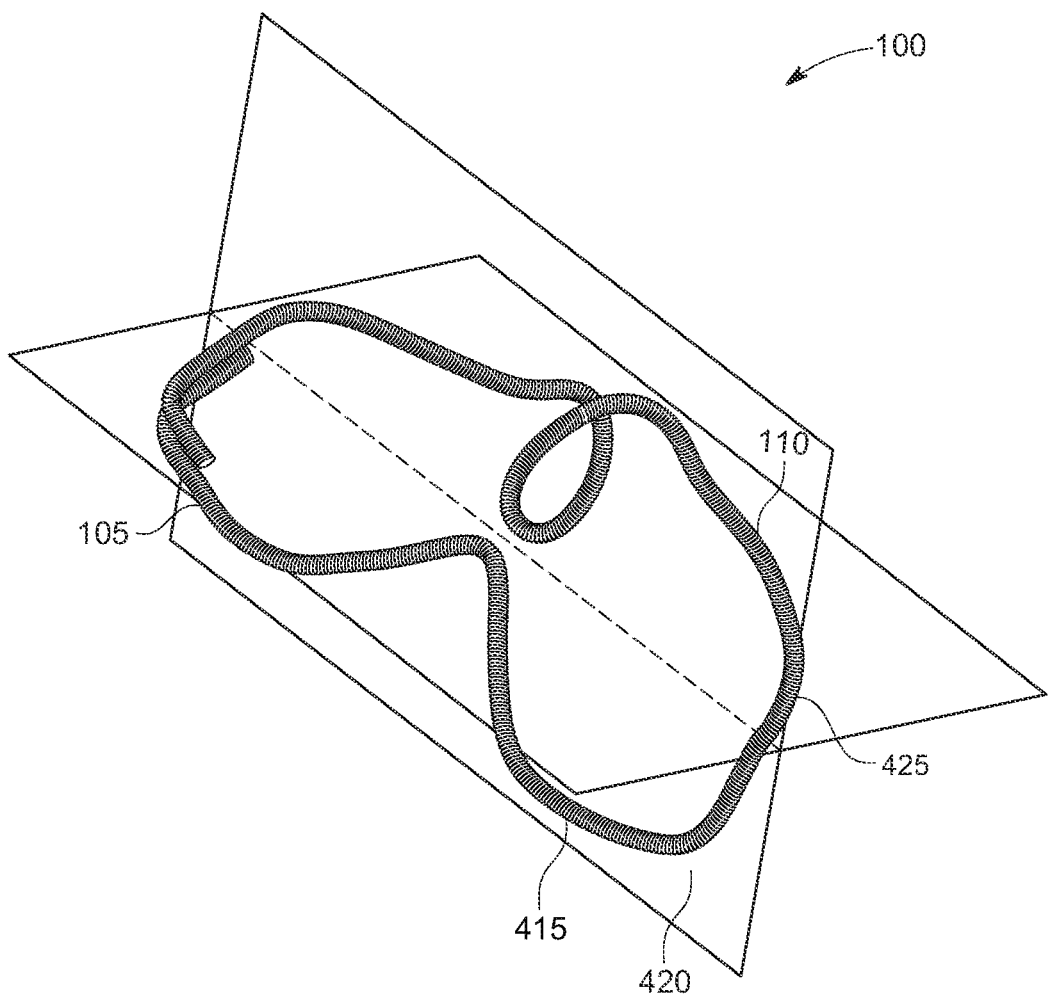
FIG. 4 illustrates an endovascular coil with one or more stress points in accordance with some embodiments of the present disclosure.

FIG. 4 illustrates coil 100 in accordance with some embodiments of the present disclosure. Coil 100 can have one or more stress points (corners or abrupt transitions) in one or more of the loops. For example, loop 310 can have stress points 415, 420, and 425 induced into the coil. This can be done during the heat shaping process and by using a mandrel with sharper edges where the stress points are wrapped against. Each of the stress points can have a bending radius (r) that is 0.001 to 0.5 of the radius of loop 305 or 310. For example, one of the stress points can have a bending radius of 0.1×r or 0.2×r.

Figure 5:
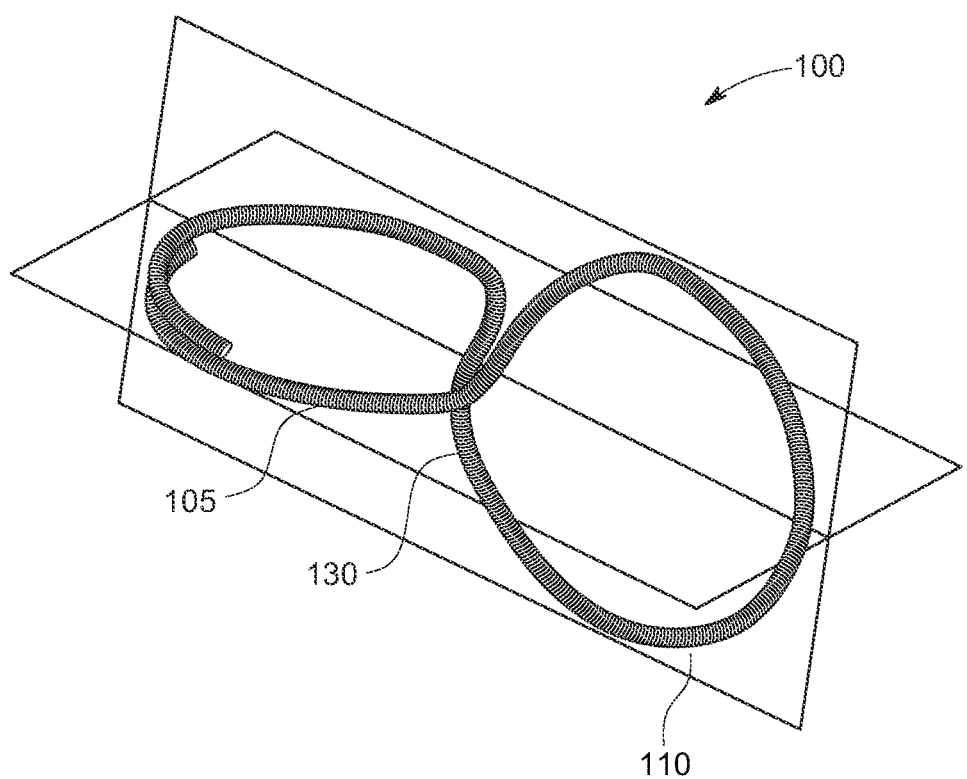
FIG. 5 illustrates an endovascular coil with an overlapping (touching) transition area in accordance with some embodiments of the present disclosure.

FIG. 5 illustrates coil 100 with a closed loop architecture in accordance with some embodiments of the present disclosure. Coil 100 includes a transition or inflection area 131 where a portion of loop 105 touches a portion of loop 110 to close loops 105 and 110. Additionally, coil 100 can have a clockwise (CW) and counter clock-wise (CCW) path. For example, loop 105 has a CW path and loop 110 has CCW path. Coil 100 can also have an open loop design where the loops do not touch each other as shown in FIG. 1A.

Figure 6:
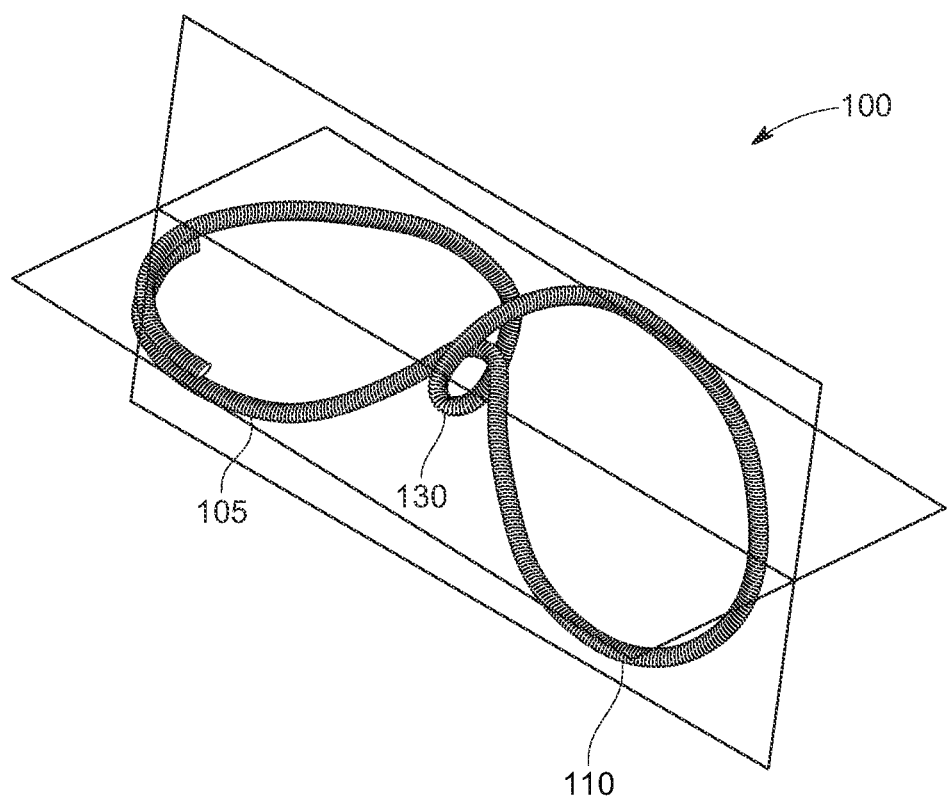
FIG. 6 illustrates an endovascular coil with an non-overlapping transition area in accordance with some embodiments of the present disclosure.

FIG. 6 illustrates coil 100 in accordance with some embodiments of the present disclosure. As shown, coil 600 has a closed loop architecture where loops 105 and 110 are closed loops. Additionally, loops 105 and 110 are rotated about each other at transition region 131 such that both loops have a clockwise path.

Figure 7A:
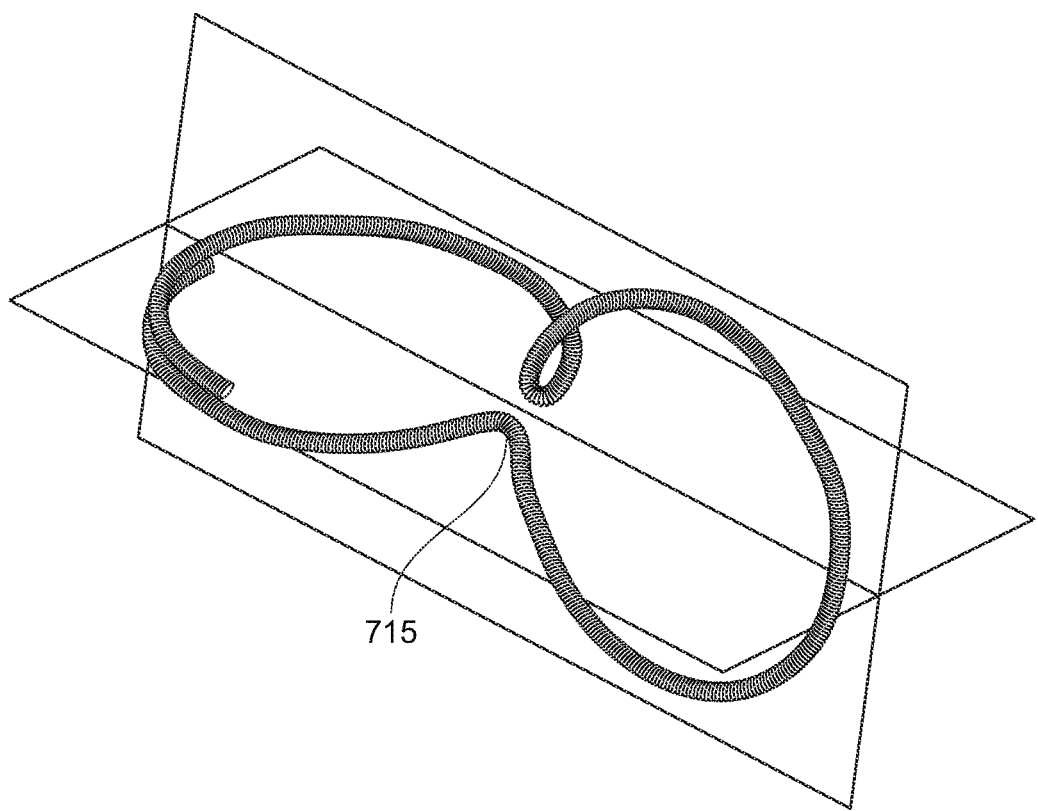
FIGS. 7A and 7B illustrate coils with different type of transition areas in accordance with some embodiments of the present disclosure.
Figure 7B:
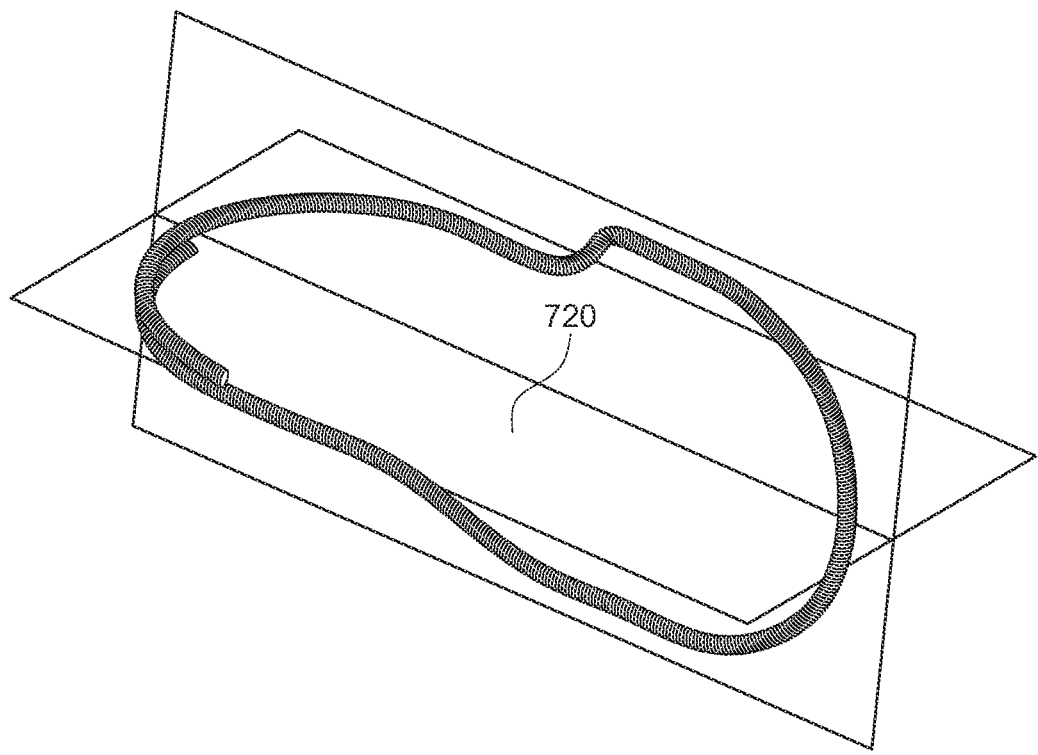

FIGS. 7A and 7B illustrate examples coils 100 with different shape at the transition areas in accordance with some embodiments of the present disclosure. As shown, transition area 715 is tighter and smaller than transition area 720.

Each of the framing coils described above can have repeating loops on one or more planes (e.g., plane 115 or plane 120). In some embodiments, applying the disclosed relationships onto subsequent loop pairings using different plane-pairing (e.g., plane 2/plane 3, plane 3/plane 4) to create the intended length of the coil, which can be between 1 cm to 80 cm. The coil shape may leverage a combination of closed/open, intersect/non-intersect and CW/CCW strategies throughout the entire length of the coil. It should be noted that coils 250 and 300 can also one or more features and attributes of coil 100 as described in FIGS. 1A, 1B, 4, 5, 6, 7, and 8.

FIG. 8 illustrates an exemplary full length endovascular coil 800 with one or more features and attributes of coils 100, 250, and 300 as described above. Coil 800 includes 4 loops in upper portion 805 and 3 loops in lower portion 810. However, coil 800 can be fabricated to have any number of loops in each of the upper and lower portions 805, 810. As shown, the loops in lower portion 810 are rotated about longitudinal axis 815 at a desired degree of rotation, which can be 45 degrees.

Figure 9:
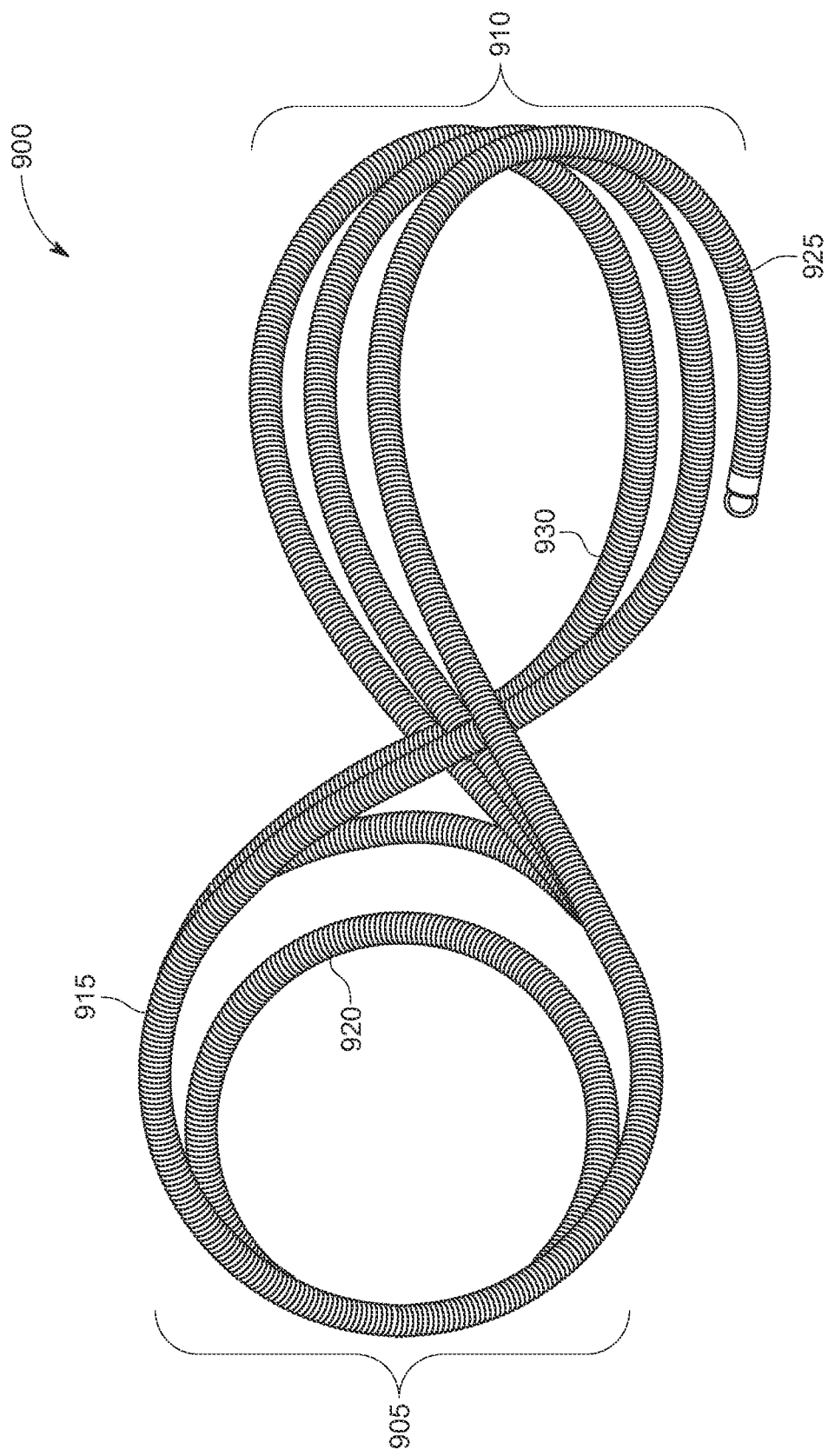
FIG. 9 illustrates another twisted figure 8 endovascular coil having multiple stacked loops in accordance with some embodiments of the present disclosure.

FIG. 9 illustrates an exemplary full length endovascular coil 900 with one or more features and attributes of coils 100, 250, and 300. Coil 900 includes a first portion 905 and a second portion 910. First portion 905 includes two or more loops 915, 920. The two or more loops 915, 920 can have the same loop diameter. In some embodiments, one of the two or more loops 915, 920 has a smaller diameter than other loops of first portion 905. Similarly, second portion 910 includes two or more loops 925, 930. The two or more loops 925, 930 can have the same or different loop diameter. Additionally, second portion 910 can consist of a coil wire with different attributes (e.g., outer diameter, stiffness, cross-sectional shape, fibrous hair) than the coil wire of first portion 905. In some embodiments, two or more final loops of second portion 910 can be made with a coil wire with different attributes such as, but not limited to, smaller diameter, different cross-sectional shape, and different material.

Figure 10A:
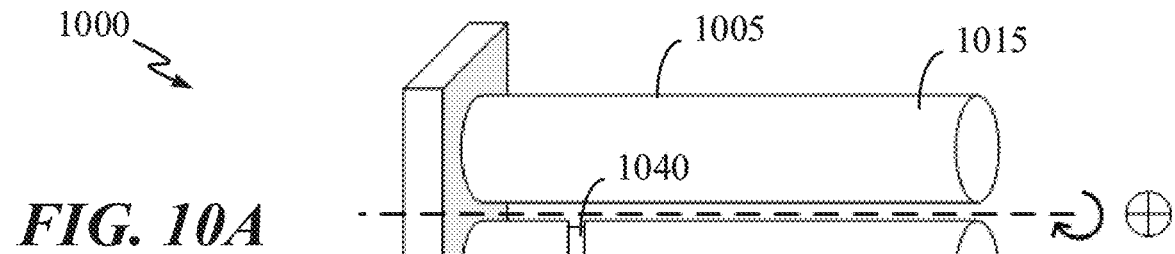
FIG. 10A-10H illustrate a process for fabricating a twisted figure 8 endovascular coil in accordance with some embodiments of the present disclosure.

FIGS. 10A-H illustrates a process 1000 for winding the twisted figure 8 coil (e.g., 100, 250, 300, 800, 900) in accordance with some embodiments of the present disclosure. As shown in FIG. 10A, mandrel 1005 includes a first rod 1010, a second rod 1015, and a mandrel base 1020. During the coil fabrication process, both rods 1010, 1015 can be secured to mandrel base 1020. Once the wire wrapping process is completed, mandrel base 1020 can be removed to enable rods 1005, 1010 to rotate with respect to each other about center point of the coil wrappings (this process is further described below).

Process 1000 starts in FIG. 10A where an end portion of a wire 1025 of coil wire 1030 is secured around post 1035. Once end portion 1005 is secured to post 1035, coil wire 1030 is nudged into groove 1040 (optional), which creates a first loop with a smaller loop diameter than subsequent loops. Groove 1040 can include a transition area (not shown) where the groove's bottom slowly ramps up to the same level as the outer surface of rod 1010. The distal end of coil wire 1030 (not shown) is secured to a tensioning mechanism or a weight. This helps keep tension and creates a tight wrap around rod 1010 or 1015.

Figure 10B:
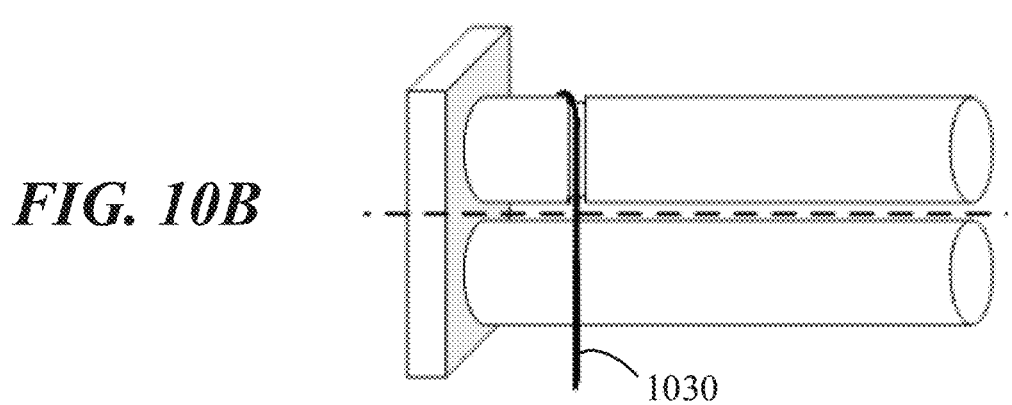
Figure 10C:
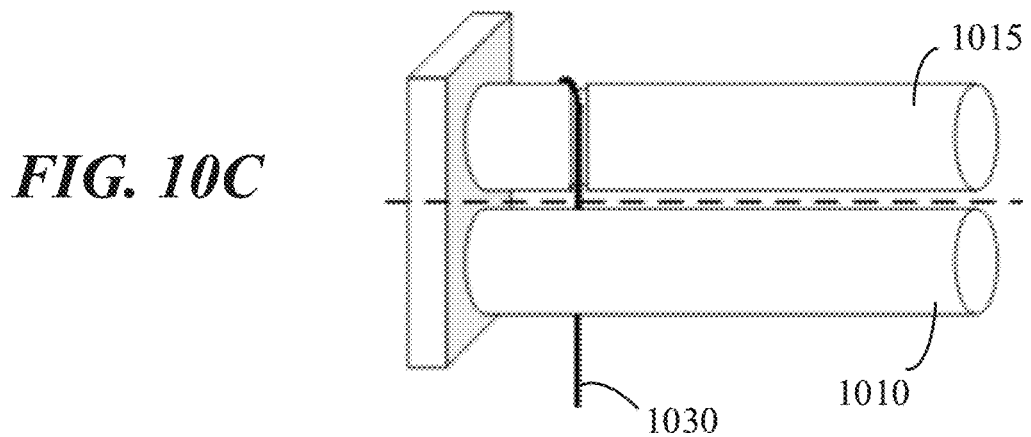
Figure 10D:
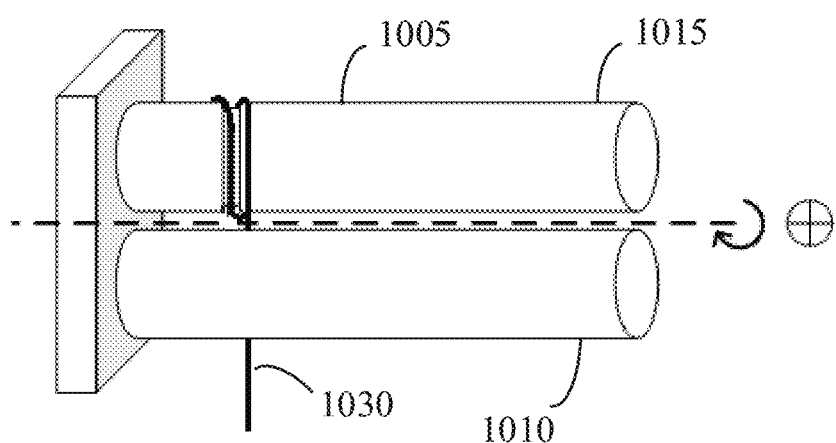
Figure 10E:
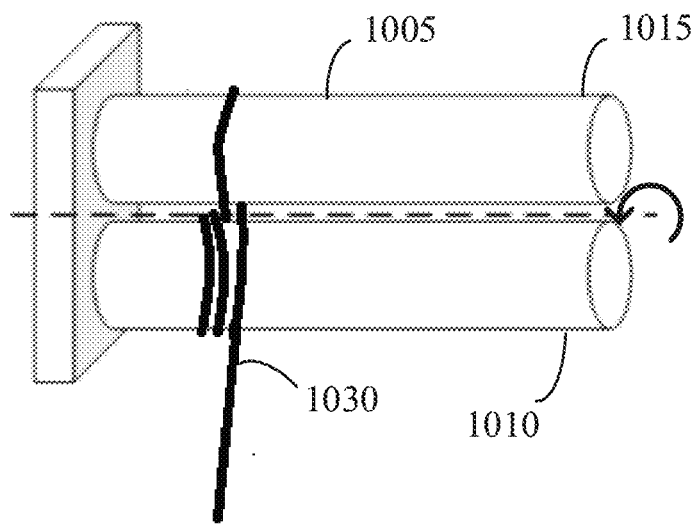
Figure 10F:
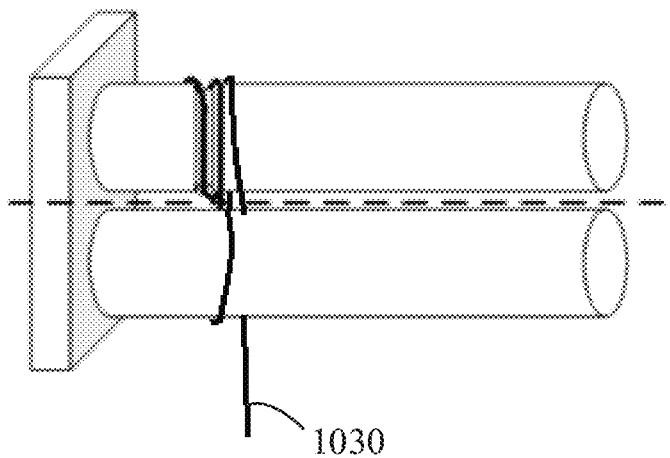

In FIG. 10B, mandrel 1005 is rotated into the page (as defined by the right hand rule with the thumb pointing to the left) by 180 degrees. This action pulls up coil 1030 leaving coil wire 1030 hanging as shown. In FIG. 10C, coil wire 1030 is placed between rods 1010 and 1015. Next, in FIG. 10D, mandrel 105 is rotated into the page by 360 degrees and coil wire 1030 is again placed between rods 1010 and 1015. Next, in FIG. 10E, mandrel 1005 is rotated out of the page (right thumb pointing to the right) and coil wire 1030 is placed between rods 1010 and 1015. To create the next wrap in FIG. 10F, mandrel 1005 is rotated in the opposite direction (into the page) and again coil wire 1030 is placed between rods 1010 and 1015 before the next rotation of mandrel 1005. The procedures shown in FIGS. 10E and 10F are repeated (e.g., mandrel is rotated in opposite direction every other time and the coil wire is threaded between rods 1010 and 1015 after each rotation) until a desired number of loops are created. Although the coil wrappings are shown to be loosely spaced, in practice the coil wrappings are tightly wrapped and are adjacent to each other with little to no room between each coil wrapping.

Figure 10G:
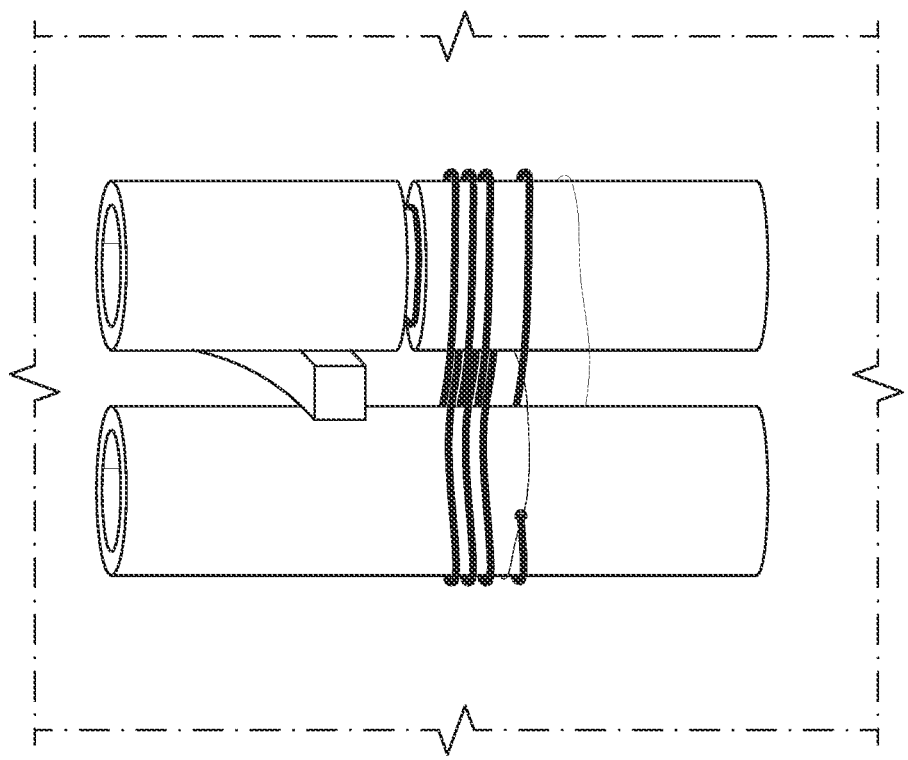
Figure 10H:
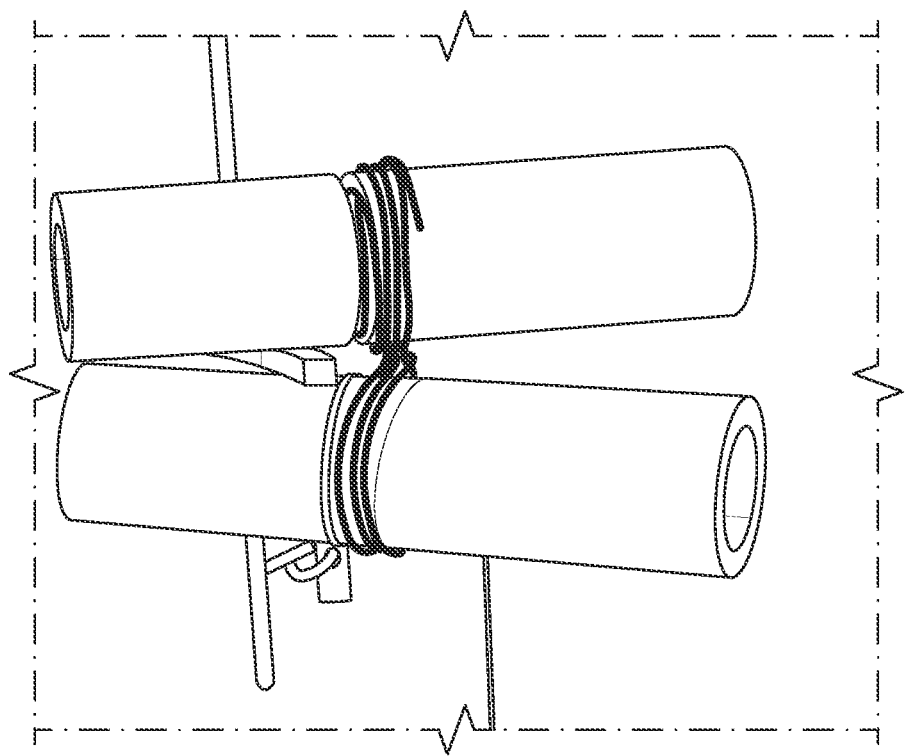

FIG. 10G illustrates a coil with a number of desired loops wrapped around rods 1010 and 1015. Once the desired number of loops is created, mandrel base 1020 can be removed to allow for rods 1010 and 1015 to rotate with respect to each other about a center point 1050, which is approximately the center of all the loops wrapped around rods 1010 and 1015. FIG. 10H shows rods 1010 and 1015 rotated about center point 1050. The angle of rotation can vary depending upon the design specification. However, the angle of rotation can be any angle between 1-179 degrees. In some embodiments, the angle of rotation is 45 degrees. A rotation setting and locking mechanism (not shown) can be used to set the rotation angle and also to secure rods 1010 and 1015 at the desired angle of rotation. The entire mandrel and the rotation setting & locking mechanism assembly is then placed into an oven for a heat set procedure. The heat setting process sets the shape of the secondary configuration (e.g., minimum energy state) of coil 100 to the same shape as shown in FIG. 10H without the rods.

For the heat setting procedure, the oven can be set at 650-750 degrees Celsius, and the bake time can be 20-40 minutes. In some embodiments, the bake time is 30 minutes, and the temperature of the oven is set at 700 degrees Celsius. Alternatively, coil 100 can be heat treated at 735 degrees Celsius. Although FIGS. 10A-10H describe specific routing patterns used to create a figure 8 pattern around rods 1010 and 1015 of mandrel 1005, other routing patterns are possible and are contemplated as long as multiple figure 8 patterns are created around rods 1010 and 1015. For example, mandrel 1005 can be stationary while coil wire 1030 are manipulated around rods 1010 and 1015 to create multiple figure 8 patterns. Once this is done, one of the rods can be rotated with respect to the other rod about a point of rotation, which can be substantially along a longitudinal axis of one of the figure 8 patterns.

Figure 11A:
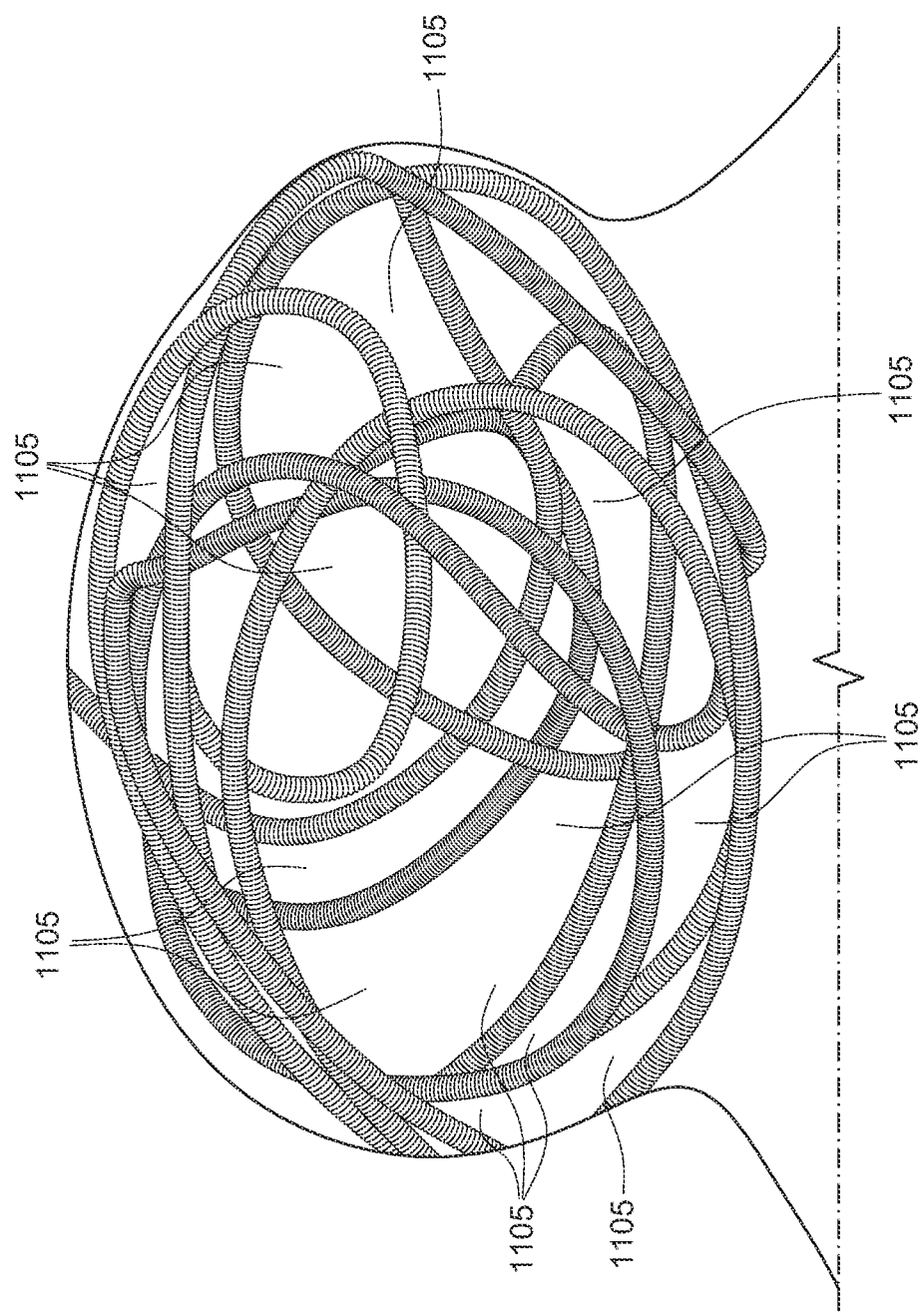
FIGS. 11A and 11B illustrate the packing behaviors of two different conventional coils.
Figure 11B:
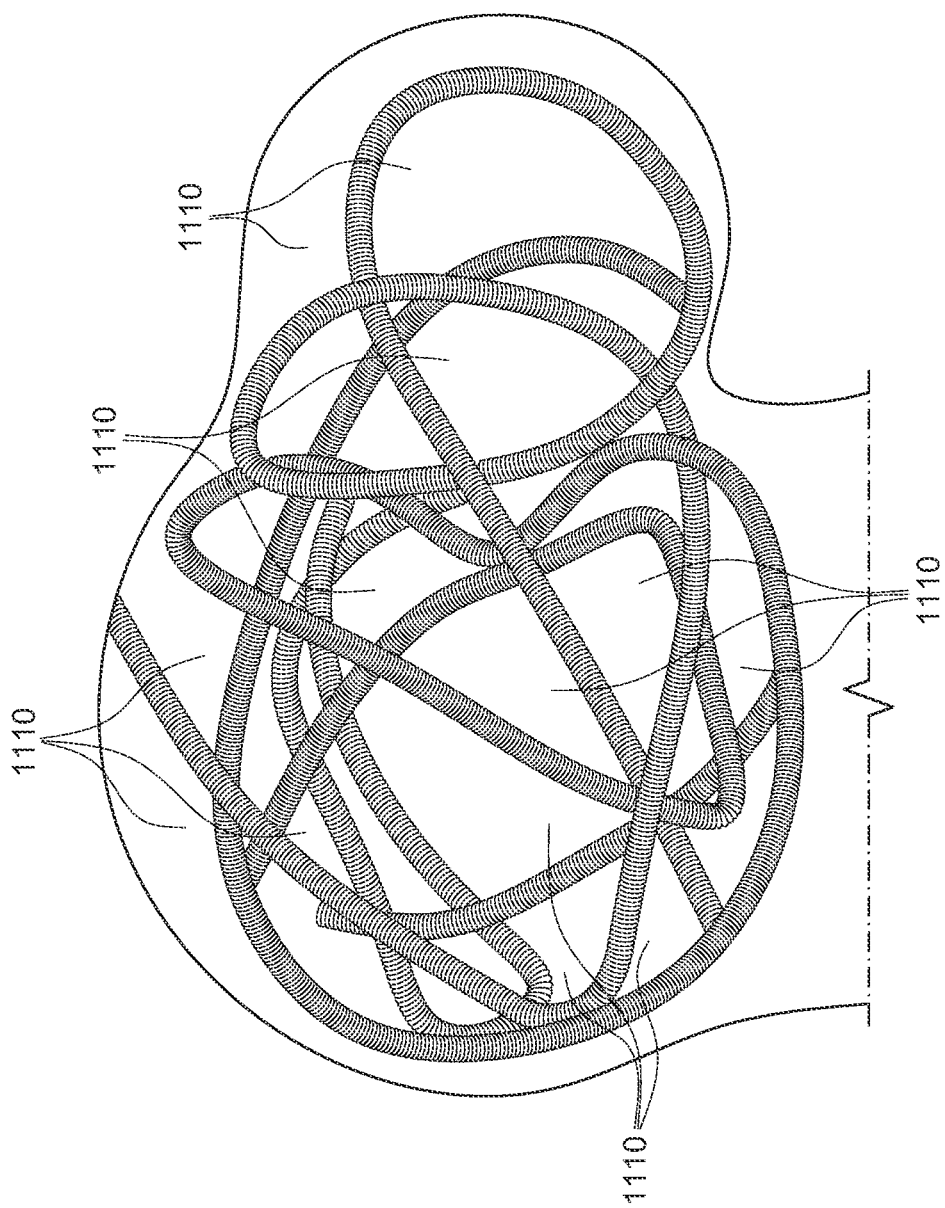
Figure 12:
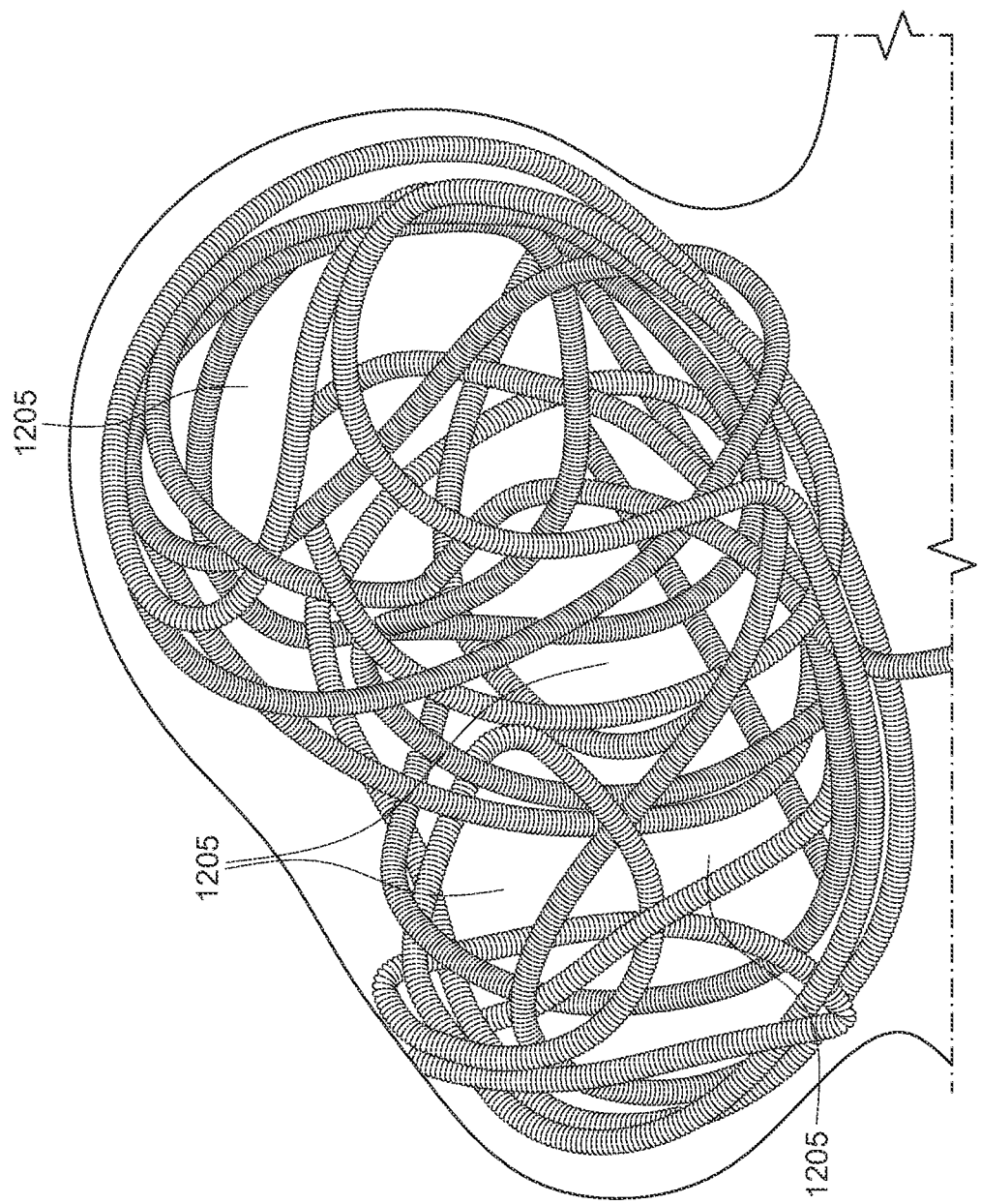
FIG. 12 illustrate the packing behavior of the twisted figure 8 endovascular coil in accordance with some embodiments of the present disclosure.

FIG. 11A-B illustrate how conventional coils fill an irregularly shaped aneurysm. In FIG. 11A, the conventional coil leaves a lot of open spaces 1105. Similarly, in FIG. 11B, another conventional coil leave even more and bigger open spaces within the aneurysm. Here, both of the coils in FIGS. 11A and 11B are essential the same length. FIG. 12 shows how the twisted figure 8 coil (e.g., 100, 250, 300) as described above fills the aneurysm. In contrast to FIGS. 11A and 11B, the twisted figure 8 coil leaves very little open spaces within the aneurysm. The number of spaces 1205 is much less and the number of spaces 1105 and 1110 in FIG. 11A and FIG. 11B, respectively. The coil length of the twisted figure 8 coil in FIG. 12 is the same as the length of the coils in FIGS. 11A and 11B.

In some embodiments, the twisted figure 8 coil (e.g., 100, 250, 300, 800, 900) disclosed above can have a distal portion made with a different coil wire material. The distal portion can be welded onto the end of proximal portion, which can be longer in length than the distal portion. The distal portion can have a length that is 5 to 7 times shorter than the proximal portion. The length of the distal portion can be appropriately selected such that the length is sufficient to create 2 or more loops.

The wire of the distal portion can have a smaller outer diameter than the wire of the proximal portion. In some embodiments, the outer diameter of the wire of distal portion is 0.002" inch. For the heat setting procedure, the proximal portion of the twisted figure 8 coil can be heat treated (set) prior to welding on the distal portion. Once the distal portion is welded on, the entire coil assembly (proximal and distal portions) can be heat treated again at a temperature ranging from 70-90 degrees Celsius for 4-6 minutes. In some embodiments, the entire coil assembly can be heat treated again at a temperature of 80 degrees Celsius for approximately 5 minutes. This helps shrink the diameter of the distal loops (formed by the welded on distal portion) by 20%. In other words, the diameter of the distal loop is 80% of the main loop.

Coil 900 can be configured to have a 50/50 distribution over two 3D spaces. In this way, a bi-lobed aneurysm can be effectively filled by framing coil 800.

The complex shape disclosed in this invention is intended to provide the ability to effectively treat spherical and/or non-spherical (e.g. elliptical, multi-lobed) aneurysms while minimizing risk of loop protrusion into the patient artery. The unique attributes, parameters and relationships identified present a unique opportunity to realize improved performance in areas such as achievable packing density, delivery friction, coil distribution uniformity, neck coverage, ability to minimize compartmentalization and long term stability as compared to existing coil designs. Table 1 below lists performance advantages utilizing key factors (e.g. attributes, parameters and/or relationships) derived from experimental data.

TABLE 1

Alignment of factors with advantages.

| # | Factor (attribute, parameter and/or relationship) | Advantage |
|---|---|---|
| 1 | Index angle between loops (1-179 degrees) | Ability to evenly seek three dimensional space more effectively |
| 2 | Paired loop end-to-end length, common axis | Ability to evenly seek three dimensional space more effectively in irregularly shaped aneurysms |
| 3 | Open or closed loop configuration | Manage compartmentalization |
| 4 | Shape of loops | Ability to manage friction, contribute to space seeking performance |
| 5 | Degree of curvature/twist at "waist" | Ability to evenly seek three dimensional space more effectively, prevent coil protrusion in spherical aneurysms |
| 6 | Undulating loops | Assist with directing coil |

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the following detailed description are presented in terms of algorithms and symbolic representations of operations on data bits within a computer memory. These algorithmic descriptions and representations are the methods used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared or otherwise manipulated. It has proven convenient at times, principally for reasons of common usage, to refer to these signals as bits, values, elements, symbols, characters, terms, numbers or the like.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats.

The invention claimed is:

1. An embolic coil consisting essentially of:
   a wire formed into a coil having the shape of a stacked plurality of at least 3 twisted figure 8 configurations around a mandrel consisting essentially of a parallel set of rods, wherein, each figure 8 configuration in the plurality has
      a respective first loop;
      a respective second loop;
      a respective inflection area between the respective first loop and the respective second loop;
      a respective focal point; and,
      a respective common axis of both the respective first loop and the respective second loop on the mandrel,
   such that the stack of figure 8 configurations has
      all respective first loops in a single stack;
      all respective second loops in a single stack;
      all respective inflection areas in a single stack;
      all respective focal points in a single stack; and,
      all respective common axes in a single stack;
   wherein,
   the coil includes a desired offset angle ranging from 5 degrees to 45 degrees induced from a rotation between the stack of the respective first loops and the stack of respective second loops, the rotation
      (i) occurring
         on the mandrel by rotating the rods of the mandrel away from the parallel in an amount ranging from the 5 degrees to the 45 degrees away from the parallel at the region between the single stack of all respective first loops and the single stack of all respective second loops, each of the respective first loops having it's respective second loop (i) initially on substantially the same plane as the respective first loop before the rotation and (ii) at the desired offset angle after the rotation; and,
         at the stack of the respective focal points in the stack of respective inflection areas and around the stack of the respective common axes, and (ii);
      wherein, the rotation creates the twisting of the shape of the stacked plurality of figure 8 configurations into the stacked plurality of twisted figure 8 configurations;
   the shape of the wire is heat set into the stacked plurality of twisted figure 8 configurations at the desired angle of rotation; and,
   the coil effectively supports irregular-shaped and multi-lobe aneurysms after removal from the mandrel and insertion into the aneurysms.

2. The coil of claim 1 produced using a process that includes
   wrapping the wire in a figure 8 pattern around the pair of parallel rods, the parallel rods including a first rod having a first central axis and a second rod having a second central axis, the wrapping forming the plurality of stacked figure 8 configurations, each figure 8 configuration in the plurality having the respective first loop, the respective second loop substantially on the same plane as the respective first loop, the respective inflection area between the respective first loop and the respective second loop, the respective focal point in the respective inflection area, and the respective common axis of both the respective first loop and the respective second loop, such that the stack of figure 8 configurations has
       all respective first loops in a single stack;
       all respective second loops in a single stack;
       all respective inflection areas in a single stack;
       all respective focal points in a single stack; and,
       all respective common axes in a single stack;
   rotating the central axis of the first rod relative to the central axis of the second rod at the stack of the respective common axes to the desired offset angle ranging from 5 degrees to 45 degrees, the rotating occurring at the stack of respective focal points in the stack of the respective inflection areas and around the stack of the respective common axes, twisting the shape of the stacked plurality of figure 8 configurations into the stacked plurality of twisted figure 8 configurations; and,
   heat setting the shape of the formed wire into the stacked plurality of twisted figure 8 configurations at the desired angle of rotation.

3. The coil of claim 2, wherein the heat setting includes applying a temperature in the range of 650° F. to 750° F. for a time in the range of 20 minutes to 40 minutes.

4. The coil of claim 2, wherein the rotating includes selecting the desired offset angle from the group consisting of 30, 35, 40, 45, and 50 degrees.

5. The coil of claim 2, wherein the rotating includes selecting the desired offset angle from the group consisting of 30, 35, 40, and 45 degrees.

6. The coil of claim 1, wherein the second loop comprises undulating tracing pattern that dips above and below a primary plane of the first loop.

7. The coil of claim 1, wherein the first loop comprises a first cross-section and the second loop comprises a second cross-section, wherein the first and second cross-section are different.

8. The coil of claim 1, wherein the wire has more than one physical attribute along the length of the wire, the attribute selected from the group consisting of a wire stiffness, a cross-sectional shape, a diameter, or an external feature.

9. The coil of claim 1, wherein a mandrel includes the first rod and the second rod, and the mandrel has a shape that induces one or more stress points into the endovascular coil.

10. The coil of claim 9, wherein a stress point has a bending radius of between 0.001 to 0.5.

11. The coil of claim 1, wherein the wire is heat set at a temperature in the range of 650° F. to 750° F. at a time in the range of 20 minutes to 40 minutes.

12. The coil of claim 1, wherein the rotating includes selecting the desired offset angle from the group consisting of 30, 35, 40, 45, and 50 degrees.

13. The coil of claim 12, wherein the rotating includes selecting the desired offset angle from the group consisting of 30, 35, 40, and 45 degrees.

* * * * *